(12) United States Patent
Ziolo et al.

(10) Patent No.: US 8,556,942 B2
(45) Date of Patent: Oct. 15, 2013

(54) OCCIPITO-CERVICAL FIXATION ASSEMBLY AND METHOD FOR CONSTRUCTING SAME

(75) Inventors: Tara Ziolo, Hewitt, NJ (US); Stephen Termyna, Boonton, NJ (US)

(73) Assignee: Blackstone Medical, Inc., Lewisville, TX (US)

( * ) Notice: Subject to any disclaimer, the term of this patent is extended or adjusted under 35 U.S.C. 154(b) by 0 days.

(21) Appl. No.: 13/341,587

(22) Filed: Dec. 30, 2011

(65) Prior Publication Data

US 2013/0172938 A1 Jul. 4, 2013

(51) Int. Cl.
*A61B 17/80* (2006.01)

(52) U.S. Cl.
USPC .......................... 606/280; 606/286

(58) Field of Classification Search
USPC ........... 606/250–253, 278, 279, 280–299, 70, 606/71
See application file for complete search history.

(56) References Cited

U.S. PATENT DOCUMENTS

| | | | |
|---|---|---|---|
| 4,046,344 A | 9/1977 | Scanlan | |
| 5,520,689 A | 5/1996 | Schlapfer et al. | |
| 5,527,310 A | 6/1996 | Cole et al. | |
| 5,669,910 A | 9/1997 | Korhonen et al. | |
| 6,217,578 B1 | 4/2001 | Crozet et al. | |
| 6,264,658 B1 | 7/2001 | Lee et al. | |
| 6,302,882 B1 | 10/2001 | Lin et al. | |
| 6,309,390 B1 | 10/2001 | Le Couedic et al. | |
| 6,540,748 B2 | 4/2003 | Lombardo | |
| 6,547,790 B2 | 4/2003 | Harkey, III et al. | |
| 6,595,992 B1 | 7/2003 | Wagner et al. | |
| 6,699,248 B2 | 3/2004 | Jackson | |
| 6,752,807 B2 | 6/2004 | Lin et al. | |
| 6,783,526 B1 | 8/2004 | Lin et al. | |
| 6,866,664 B2 | 3/2005 | Schar et al. | |
| 7,066,938 B2 | 6/2006 | Slivka et al. | |
| 7,160,301 B2 | 1/2007 | Cordaro | |
| 7,232,441 B2 | 6/2007 | Altarac et al. | |
| 7,270,665 B2 | 9/2007 | Morrison et al. | |
| 7,344,537 B1 | 3/2008 | Mueller | |

(Continued)

FOREIGN PATENT DOCUMENTS

EP 0572790 B1 2/1996
WO 2007041085 A1 4/2007

OTHER PUBLICATIONS

International Search Report and Written Opinion, PCT/US2012/072107, 9 pages, dated Mar. 1, 2013.

(Continued)

*Primary Examiner* — Mary C. Hoffman
*Assistant Examiner* — Christina Negrellirodriguez
(74) *Attorney, Agent, or Firm* — Baker & McKenzie LLP

(57) ABSTRACT

An implantable orthopedic assembly comprises an occipital plate and one or more repositionable clamping assemblies for securing a stabilizing rod to the plate. When unlocked, the clamping assembly may be laterally and rotationally repositioned along a supporting rail. Locking occurs when a stabilizing rod is secured in the clamping assembly. The rod exerts a force upon a locking component, causing the locking component to exert a force upon the supporting rail. This force pulls a surface of the clamping assembly base into contact with the rail, effectively locking the clamping assembly base at a fixed position. The clamping assembly may further comprise a loading component to exert a stabilizing force on the locking component, keeping the clamping assembly positionally stable while adjustments are made prior to locking.

28 Claims, 11 Drawing Sheets

(56) References Cited

U.S. PATENT DOCUMENTS

| | | |
|---|---|---|
| 7,481,827 B2 | 1/2009 | Ryan et al. |
| 7,621,942 B2 | 11/2009 | Piehl |
| 7,645,294 B2 | 1/2010 | Kalfas et al. |
| 7,695,500 B2 | 4/2010 | Markworth |
| 7,717,939 B2 | 5/2010 | Ludwig et al. |
| 7,918,876 B2 | 4/2011 | Mueller et al. |
| 8,025,679 B2 | 9/2011 | Nichols et al. |
| 2003/0045874 A1 | 3/2003 | Thomas, Jr. |
| 2003/0114853 A1 | 6/2003 | Burgess et al. |
| 2003/0130661 A1 | 7/2003 | Osman |
| 2004/0133203 A1 | 7/2004 | Young et al. |
| 2005/0090821 A1 | 4/2005 | Berrevoets et al. |
| 2005/0228326 A1 | 10/2005 | Kalfas et al. |
| 2005/0228377 A1 | 10/2005 | Chao et al. |
| 2006/0058789 A1 | 3/2006 | Kim et al. |
| 2006/0064093 A1 | 3/2006 | Thramann et al. |
| 2006/0235392 A1 | 10/2006 | Hammer et al. |
| 2006/0271051 A1 | 11/2006 | Berrevoets et al. |
| 2007/0016197 A1 | 1/2007 | Woods et al. |
| 2007/0118121 A1 | 5/2007 | Purcell et al. |
| 2007/0213723 A1 | 9/2007 | Markworth et al. |
| 2008/0021456 A1 | 1/2008 | Gupta et al. |
| 2008/0086134 A1 | 4/2008 | Butler et al. |
| 2008/0091205 A1 | 4/2008 | Kuiper et al. |
| 2008/0109039 A1 | 5/2008 | Michielli et al. |
| 2008/0125781 A1 | 5/2008 | Hoffman et al. |
| 2008/0147123 A1 | 6/2008 | Schermerhorn |
| 2008/0172093 A1 | 7/2008 | Nilsson |
| 2008/0177314 A1* | 7/2008 | Lemoine ............... 606/250 |
| 2008/0177315 A1 | 7/2008 | Usher |
| 2009/0210007 A1 | 8/2009 | Levy et al. |
| 2009/0270924 A1* | 10/2009 | Wing et al. ............ 606/280 |
| 2009/0312801 A1 | 12/2009 | Lemoine et al. |
| 2010/0010541 A1 | 1/2010 | Boomer et al. |
| 2010/0094345 A1 | 4/2010 | Saidha et al. |
| 2010/0152776 A1 | 6/2010 | Keyer et al. |
| 2010/0204733 A1 | 8/2010 | Rathbun et al. |
| 2010/0222779 A1 | 9/2010 | Ziemek et al. |
| 2010/0256681 A1 | 10/2010 | Hammer et al. |
| 2010/0324557 A1 | 12/2010 | Cheema et al. |
| 2011/0190824 A1 | 8/2011 | Gephart et al. |

OTHER PUBLICATIONS

International Search Report and Written Opinion, PCT/US2012/032805, dated Aug. 3, 2012, 8 pages.

International Search Report & Written Opinion, PCT/US2012/072110, dated Mar. 15, 2013, 9 pages.

U.S. Office Action, U.S. Appl. No. 13/341,636, dated Jun. 18, 2013, 7 pages.

* cited by examiner

OCCIPITO-CERVICAL FIXATION ASSEMBLY AND METHOD FOR CONSTRUCTING SAME

TECHNICAL FIELD

The disclosed embodiments relate generally to orthopedic implantable device technology, and more specifically to implantable devices for use in stabilizing the occipito-cervical junction and the cervical spine.

BACKGROUND

In the human body, the lower back portion of the skull is known as the occiput, and the neck vertebrae located closest to the skull are known as the cervical spine. Critical neurological and vascular structures descending from the brain into the spinal column pass through the junction between the skull and the cervical spine (the occipito-cervical junction). When disease or traumatic injury threatens the stability of the cervical spine and/or the occipito-cervical junction, surgical intervention may be required to protect these critical structures.

Implantable occipito-cervical fixation systems that provide stabilization and/or promote fusion of the occipito-cervical junction are known in the art. However, existing systems may be difficult and time-consuming to adjust, and often fail to provide desirable configurability options. A need exists for an implantable occipito-cervical fixation system that simplifies and streamlines surgical placement procedures and provides greater configurability to accommodate varying patient anatomies during surgical placement.

BRIEF SUMMARY

Disclosed herein are various embodiments of an implantable orthopedic assembly generally comprising an occipital plate and one or more repositionable clamping assemblies for securing a stabilizing rod at a nonzero distance from a frictional surface of the plate. The frictional surfaces can comprise any of a variety of surfaces, including knurled metal, machined feature in metal, abrasive grit blasted metal, metal particles deposited on metal, bead blasted metal, and machined metal with surface roughness. One or more rails may extend laterally from the plate to support the clamping assemblies.

Embodiments of the clamping assembly generally comprise a base component, a body component, and a locking component. When unlocked, the clamping assembly may be laterally repositioned along the supporting rail and may also be rotationally repositioned. Locking occurs when a stabilizing rod is secured in the clamping assembly. The rod exerts a force upon the locking component, causing the locking component to exert a force upon the supporting rail. This force pulls a frictional surface of the clamping assembly base into a frictional surface of the rail, effectively locking the clamping assembly base at a fixed position. The clamping assembly may further comprise a loading component to exert a stabilizing force on the locking component, keeping the clamping assembly positionally stable while adjustments are made prior to locking.

Embodiments of the occipital plate may comprise grooves for facilitating contouring of the plate. The plate may also comprise one or more apertures for receiving bone fasteners that may secure the plate to the occiput. The apertures may be circular or non-circular, may be countersunk, and may be orthogonal or non-orthogonal to the plate. The plate may also comprise notches or other instrument interfaces for facilitating manipulation of the plate prior to and/or during placement.

Also disclosed herein are various embodiments of a method of constructing an implantable orthopedic assembly as described above. The method generally comprises positioning a locking component within the body of a clamping assembly, positioning a frictional surface of a rail against a frictional surface of the base of the clamping assembly, uniting the body with the base such that the rail contacts the locking component, and securing the base to the body. Embodiments may also comprise positioning a loading component between the locking component and the body.

DETAILED DESCRIPTION

Figure 1A:
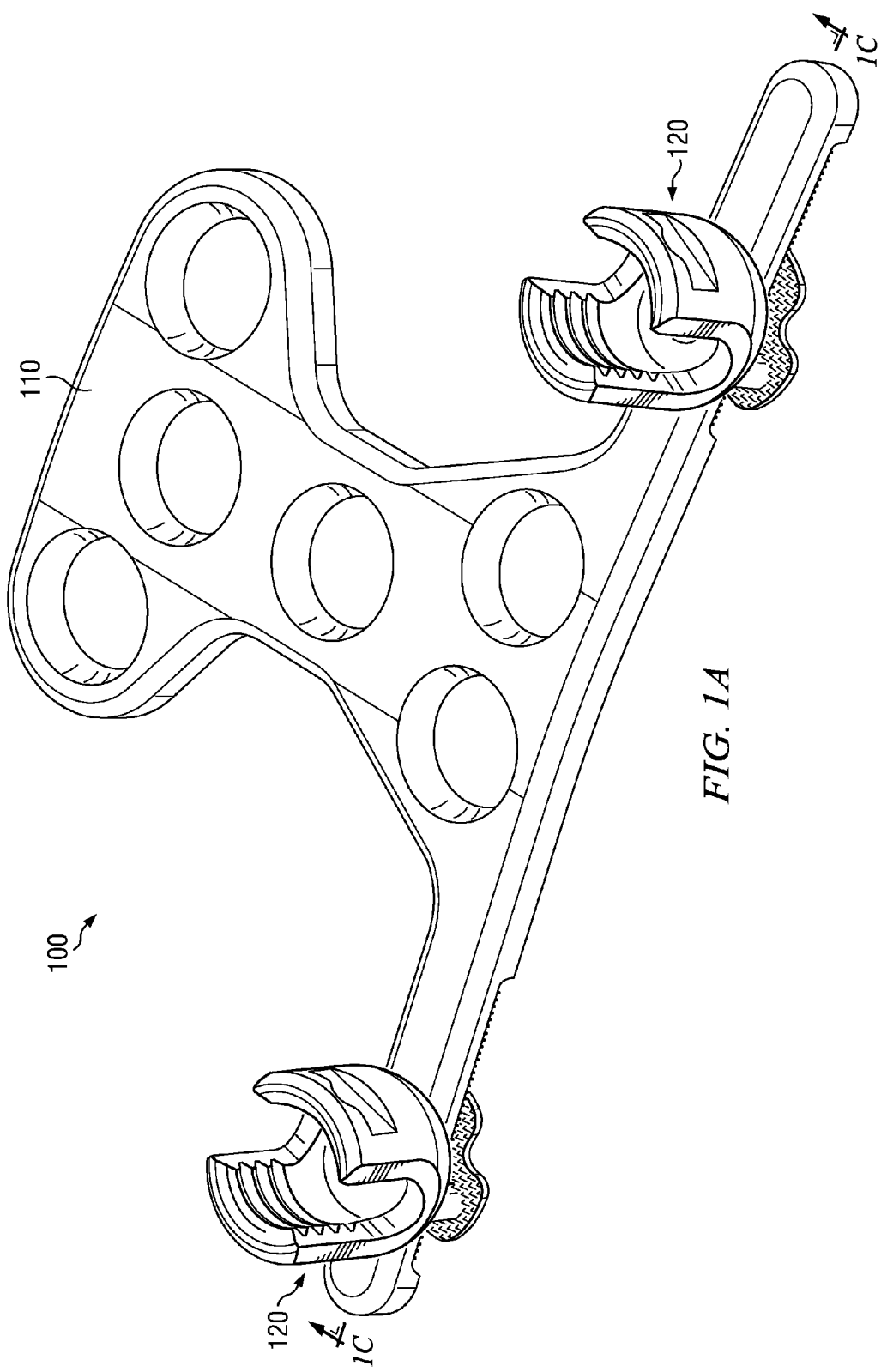
FIG. 1A illustrates a top view of an embodiment of an implantable occipito-cervical fixation assembly.
Figure 1B:
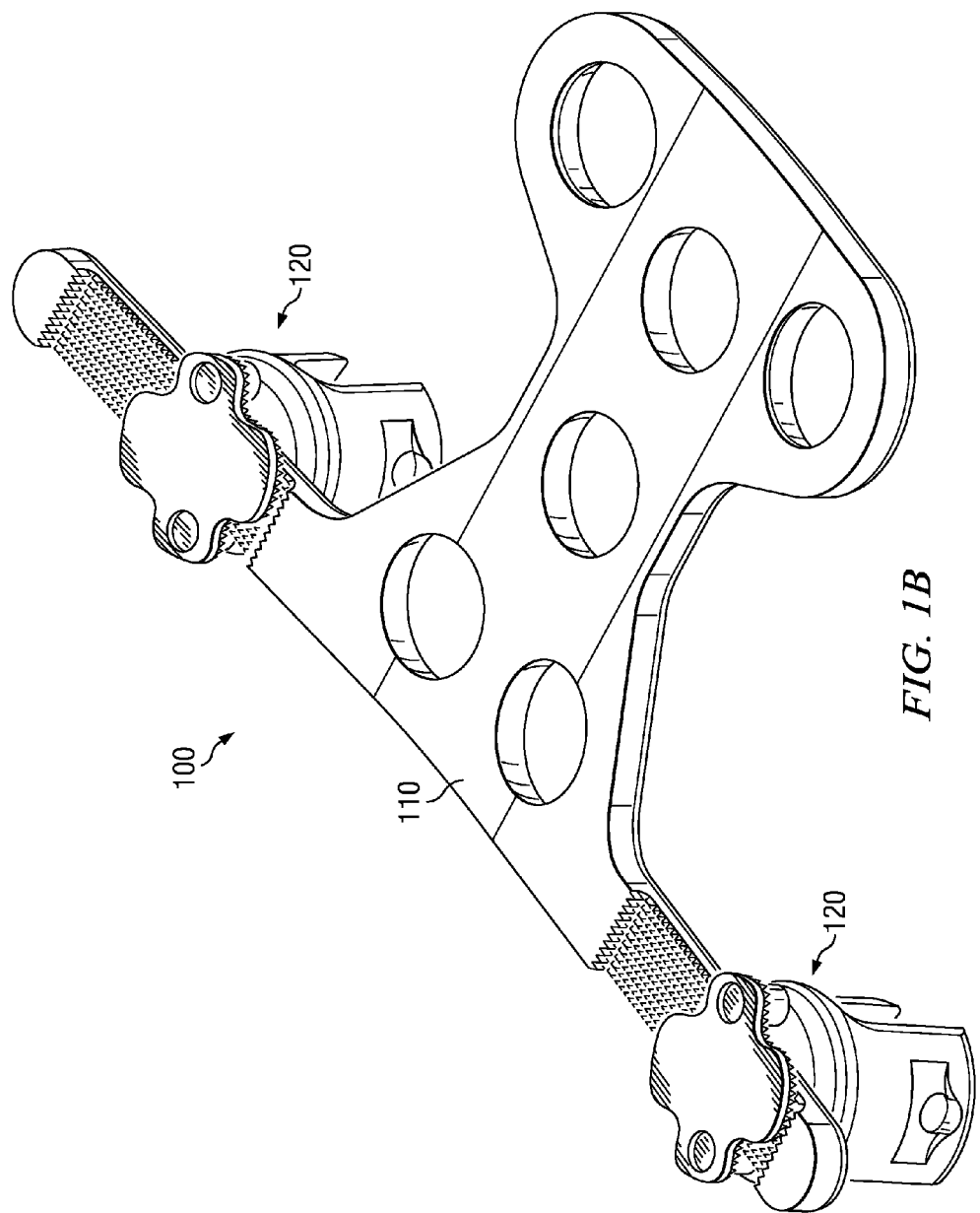
FIG. 1B illustrates a bottom view of an embodiment of an implantable occipito-cervical fixation assembly.
Figure 1C:
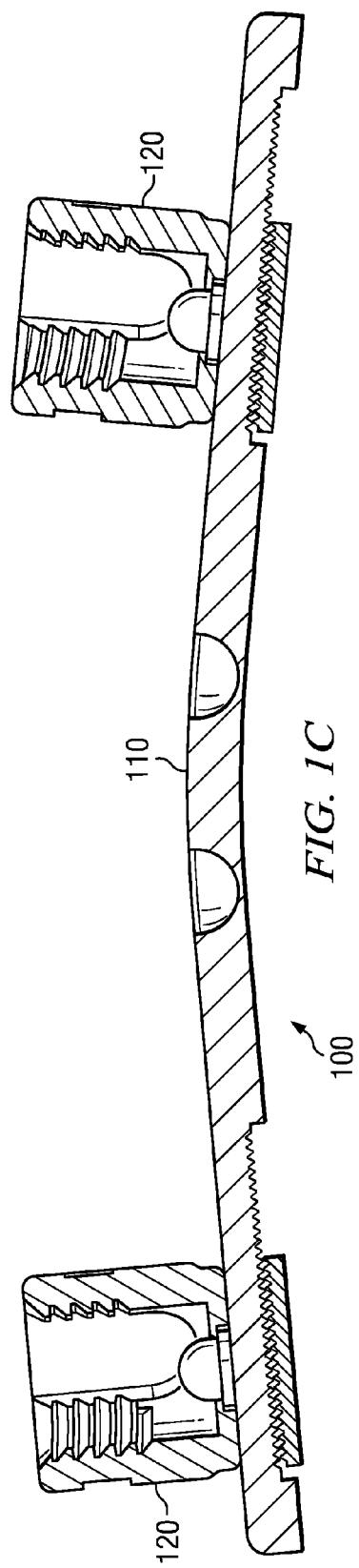
FIG. 1C illustrates a cross-sectional view of an embodiment of an implantable occipito-cervical fixation assembly.

One embodiment of an implantable occipito-cervical fixation assembly 100 is illustrated in FIGS. 1A, 1B, and 1C. A top view of this embodiment is illustrated in FIG. 1A. A bottom view of this embodiment is illustrated in FIG. 1B. A cross-sectional view of this embodiment is illustrated in FIG. 1C. Occipital plate 110 supports one or more clamping assemblies 120. Although FIGS. 1A, 1B, and 1C illustrate embodiments with two clamping assemblies, embodiments with a single clamping assembly and embodiments with three or more clamping assemblies are contemplated. Occipital plate 110 may be secured to an occiput, and a stabilizing rod (not shown) may be secured in one or more clamping assemblies 120 to provide stabilization and/or promote fusion of the occipito-cervical junction.

Each clamping assembly 120 has at least two states: locked and unlocked. In its unlocked state, each clamping assembly 120 is movably attached to a portion of occipital plate 110, and may be adjusted positionally prior to locking. For example, clamping assembly 120 may be repositioned laterally by sliding clamping assembly 120 along a portion of occipital plate 110. For another example, clamping assembly 120 may be repositioned rotationally by turning clamping assembly 120 about an axis substantially orthogonal to occipital plate 110. In its unlocked state, clamping assembly 120 may be prevented from disconnecting completely from occipital plate 110, for example by a retaining element located on occipital plate 110 or on clamping assembly 120. In some embodiments, an unlocked clamping assembly 120 may be fully disconnected from occipital plate 110. Furthermore, some embodiments of clamping assembly 120 may be configured with a loading component to positionally stabilize unlocked clamping assembly 120, allowing for more precise positioning prior to locking.

Once clamping assembly 120 is properly positioned, clamping assembly 120 may be locked in place. Once locked, clamping assembly 120 is rigidly fixed to occipital plate 110, and further lateral and rotational movement of clamping assembly 120 relative to occipital plate 110 is precluded. Locking occurs when a stabilizing rod (not shown) is inserted into clamping assembly 120. The adjustability of clamping assembly 120 relative to occipital plate 110 prior to locking, along with the simplicity of the locking procedure, allows the installation of occipito-cervical fixation assembly 100 to be quickly and easily customized to accommodate variations in patient anatomy as well as variations in desired therapeutic benefits.

Figure 2A:
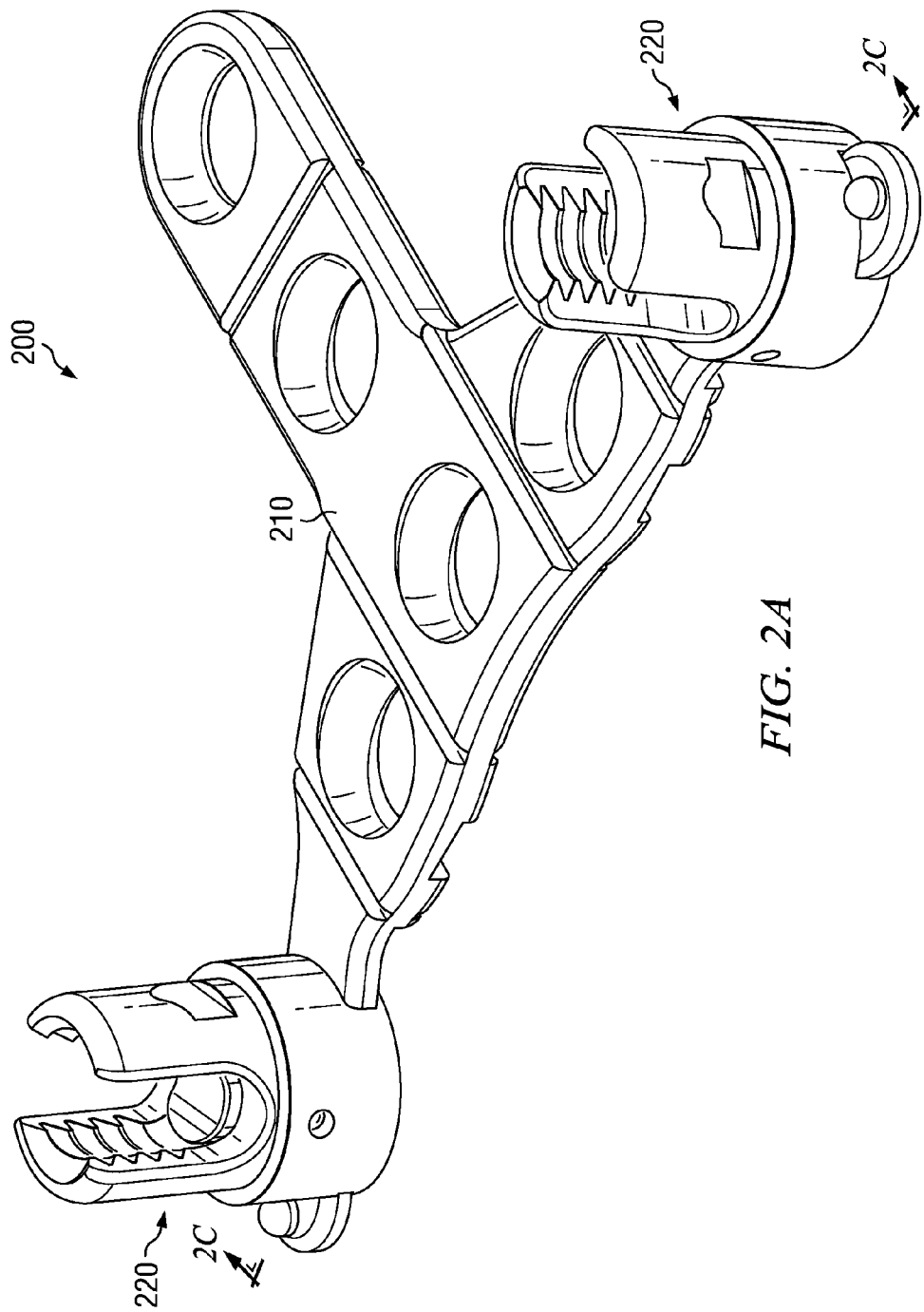
FIG. 2A illustrates a top view of an embodiment of an implantable occipito-cervical fixation assembly.
Figure 2B:
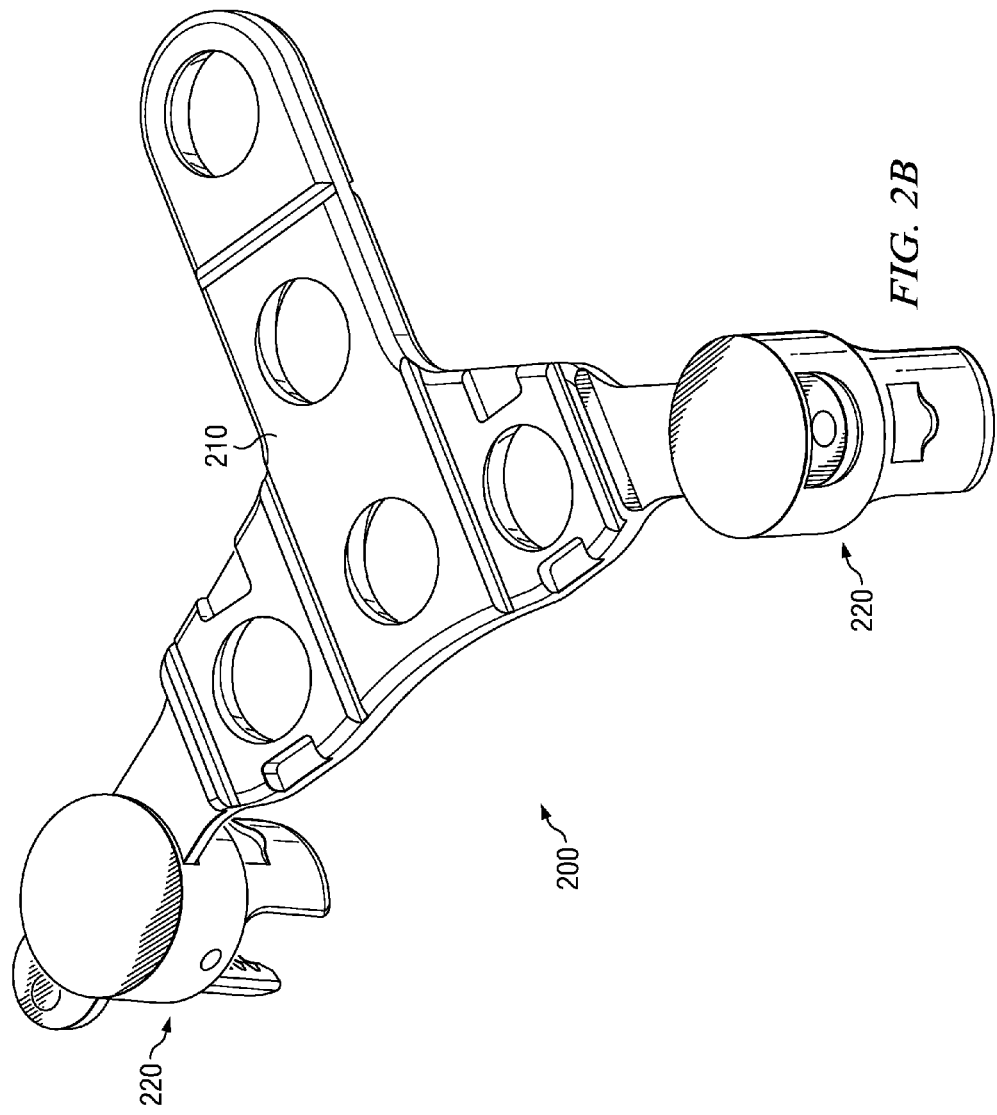
FIG. 2B illustrates a bottom view of an embodiment of an implantable occipito-cervical fixation assembly.
Figure 2C:
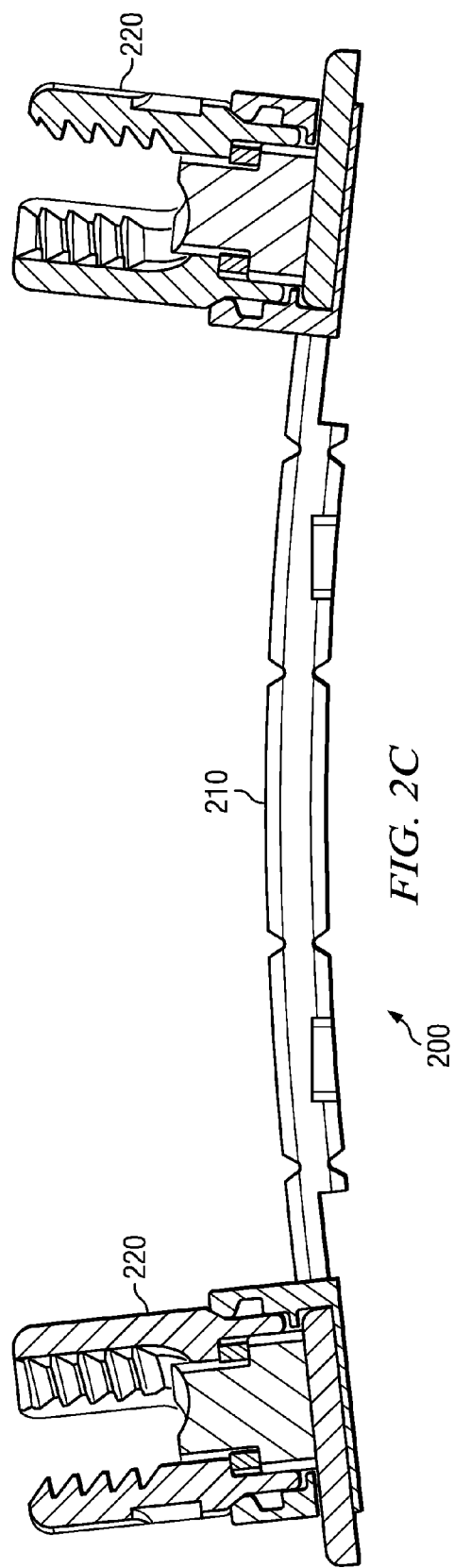
FIG. 2C illustrates a cross-sectional view of an embodiment of an implantable occipito-cervical fixation assembly.

Another embodiment of an implantable occipito-cervical fixation assembly 200 is illustrated in FIGS. 2A, 2B, and 2C. A top view of this embodiment is illustrated in FIG. 2A. A bottom view of this embodiment is illustrated in FIG. 2B. A cross-sectional view of this embodiment is illustrated in FIG. 2C. Occipital plate 210 supports one or more clamping assemblies 220. Although FIGS. 2A, 2B, and 2C illustrate embodiments with two clamping assemblies, embodiments with a single clamping assembly and embodiments with three or more clamping assemblies are contemplated. Occipital plate 210 may be secured to an occiput, and a stabilizing rod (not shown) may be secured in one or more clamping assemblies 220 to provide stabilization and/or promote fusion of the occipito-cervical junction.

Each clamping assembly 220 has at least two states: locked and unlocked. In its unlocked state, each clamping assembly 220 is movably attached to a portion of occipital plate 210, and may be adjusted positionally prior to locking. For example, clamping assembly 220 may be repositioned laterally by sliding clamping assembly 220 along a portion of occipital plate 210. For another example, clamping assembly 220 may be repositioned rotationally by turning clamping assembly 220 about an axis substantially orthogonal to occipital plate 210. In its unlocked state, clamping assembly 220 may be prevented from disconnecting completely from occipital plate 210, for example by a retaining element on occipital plate 210 or on clamping assembly 220. In some embodiments, an unlocked clamping assembly 220 may be fully disconnected from occipital plate 210. Furthermore, some embodiments of clamping assembly 220 may be configured with a loading component to positionally stabilize unlocked clamping assembly 220, allowing for more precise positioning prior to locking.

Once clamping assembly 220 is properly positioned, clamping assembly 220 may be locked in place. Once locked, clamping assembly 220 is rigidly fixed to occipital plate 210, and further lateral and rotational movement of clamping assembly 220 relative to occipital plate 210 is precluded. Locking occurs when a stabilizing rod (not shown) is inserted into clamping assembly 220. The adjustability of clamping assembly 220 relative to occipital plate 210 prior to locking, along with the simplicity of the locking procedure, allows each installation of occipito-cervical fixation assembly 200 to be quickly and easily customized to accommodate variations in patient anatomy as well as variations in desired therapeutic benefits.

Figure 3:
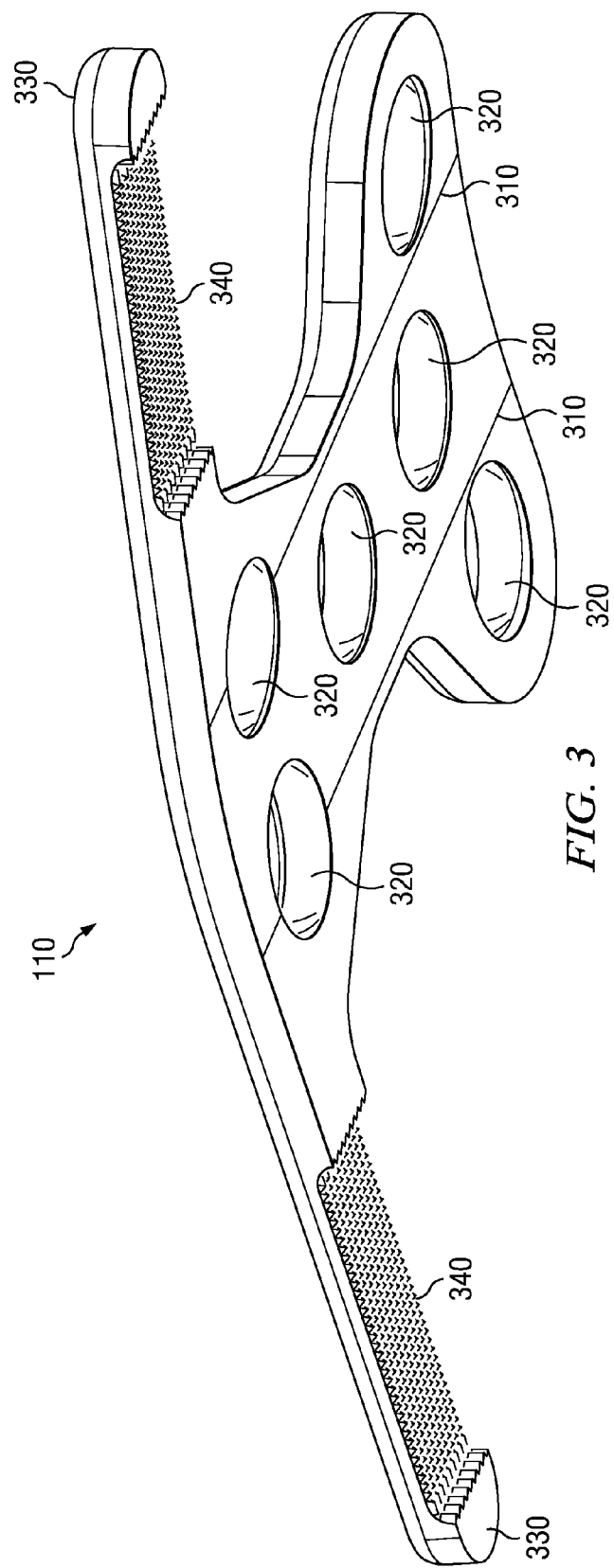
FIG. 3 illustrates an embodiment of an occipital plate component of an implantable occipito-cervical fixation assembly.

An embodiment of occipital plate 110 is illustrated in FIG. 3. Occipital plate 110 may be of any size and shape appropriate for securing to an occiput, and may be made from any material suitable for implantation into the body, such as stainless steel, titanium, ceramic, PEEK, or a composite material. Grooves 310 may be scored into the top and/or bottom surfaces of occipital plate 110 to provide for easier and more precise contouring and reshaping of occipital plate 110. Such grooves 310 may allow better correlation with the surface of the occiput. Grooves 310 may be of varying length, width, and depth, and may run laterally, longitudinally, or in any other direction. Although FIG. 3 illustrates occipital plate 110 with multiple grooves 310, an occipital plate 110 with a single groove 310 or no grooves 310 is contemplated.

As shown in FIG. 3, multiple apertures 320 may be located on occipital plate 110. One or more such apertures may be arranged in any configuration across occipital plate 110. Such apertures may penetrate both the top and bottom surfaces of occipital plate 110, and may provide for attachment of occipital plate 110 to the occiput with bone fasteners (not shown) such as bone screws, pins, staples, or any other appropriate fasteners. An aperture 320 may be circular, oval, polygonal, or any other shape about a center axis that is suitable to accommodate an appropriate fastener. Furthermore, the center axis of an aperture 320 may be orthogonal to the surface of occipital plate 110, such that a bone faster seated within aperture 320 enters the occiput orthogonally, or the center axis of an aperture 320 may be non-orthogonal to the surface of occipital plate 110, such that a bone faster seated within aperture 320 enters the occiput at an acute angle, providing for more contact between bone and fastener. In addition, aperture 320 may be countersunk such that the head of a bone fastener seated within aperture 320 is flush with or recessed from the top surface of occipital plate 110. Aperture 320 may also be counter-bored or otherwise shaped to accommodate a variety of bone fasteners. Multiple apertures 320 distributed across occipital plate 110 may be of uniform size and shape or may be of variable size and shape.

It is contemplated that occipital plate 110 may not utilize any apertures 320. In such embodiments, other methods of securing the occipital plate to the occiput are employed. For example, the occipital plate may be secured to the occiput with an adhesive, or fixation elements that penetrate the occiput may be integrated with the occipital plate, thereby eliminating the need for separate bone fasteners. Furthermore, notches or other guide features for interfacing with instruments external to occipital plate 110 may be located on occipital plate 110. Such instrument interfaces may allow a tool to be attached to facilitate placement, adjustment, and other manipulation of occipital plate 110.

As shown in FIG. 3, a rail 330 for supporting a clamping assembly extends laterally from each side of occipital plate 110. Apertures 320 may be located on the distal portion of occipital plate 110, laterally extending rails 330 may be located proximally. Although FIG. 3 illustrates an embodiment with two laterally extending rails, embodiments with a single rail and embodiments with three or more rails are contemplated. Frictional surface 340 is provided on the bottom surface of each laterally extending rail 330. In some embodiments, frictional surface 340 may be recessed relative to the bottom surface of rail 330 and/or relative to the bottom surface of occipital plate 110.

Figure 4:
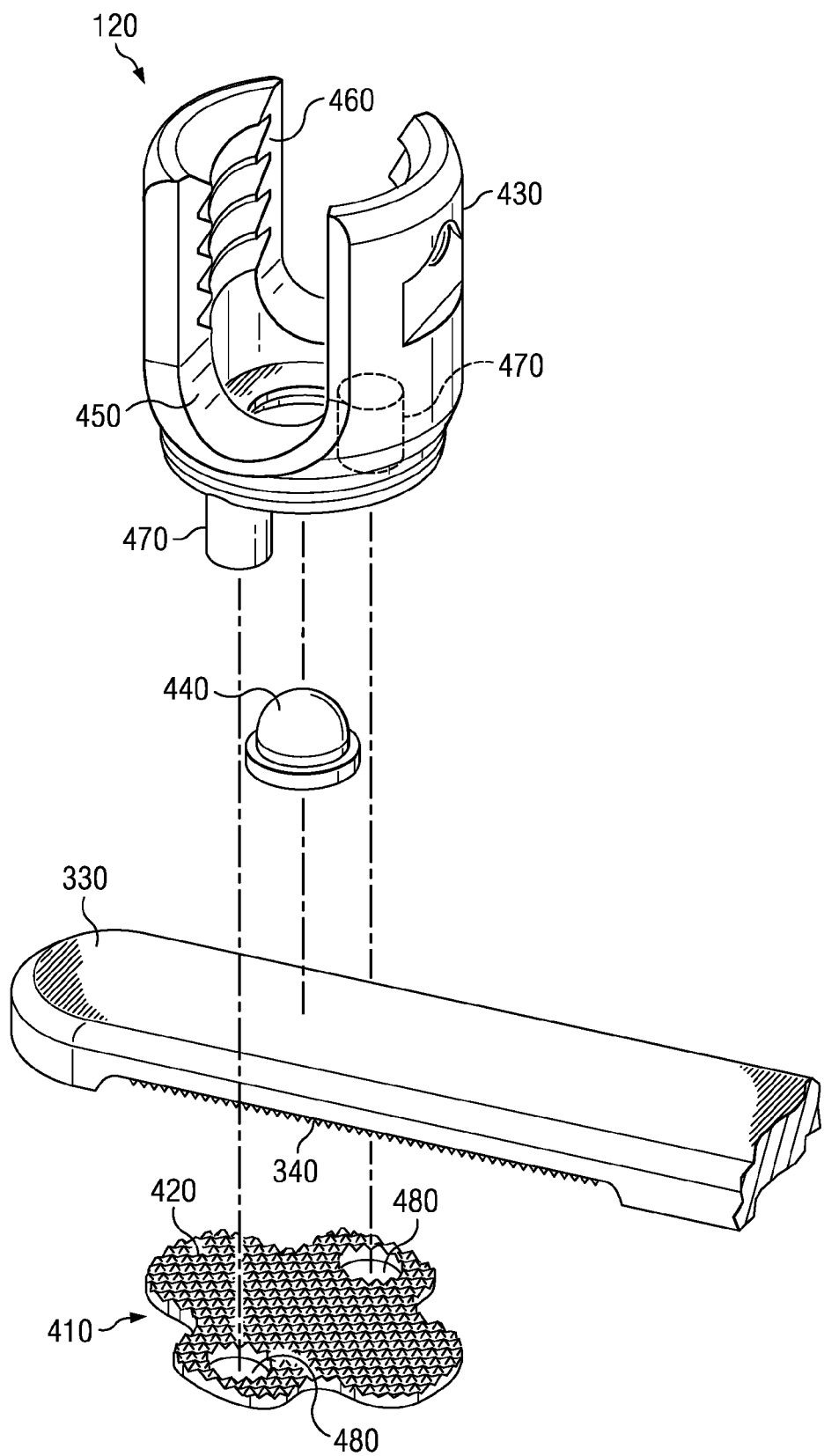
FIG. 4 illustrates an embodiment of a clamping assembly component of an implantable occipito-cervical fixation assembly.

An embodiment of clamping assembly 120 is illustrated in FIG. 4. Clamping assembly 120 may be of any size and shape appropriate for securing a stabilizing rod to an occipital plate, and may be made from any material suitable for implantation into the body, such as stainless steel, titanium, ceramic, PEEK, or a composite material. Clamping assembly base component 410 comprises frictional surface 420 and elements 480 for connecting to clamping assembly body component 430. Clamping assembly body component 430 comprises channel 450, locking threads 460, and protrusions 470 for connecting to clamping assembly base component 410. To construct an embodiment of clamping assembly 120, locking component 440 may be positioned within a receptacle of body component 430, and frictional surface 420 of clamping assembly base component 410 may be positioned against frictional surface 340 of rail 330. Body component 430 may then be united with base component 410 such that locking component 440 contacts rail 330. Body component 430 and base component 410 may then be secured together, for example by a weld applied between protrusions 470 and elements 480 or other suitable means of rigidly connecting those components; however, other suitable methods of securing body component 430 and base component 410 are contemplated. As shown in FIG. 4, one or more of the elements 470 may be positioned on opposing sides of rail 330, thereby allowing clamping assembly 120 a range of rotational movement.

As constructed, clamping assembly 120 in its unlocked state loosely encloses a portion of rail 330 and may be repositioned by sliding clamping assembly 120 along a portion of rail 330. In some embodiments, clamping assembly 120 may be repositioned at discrete points along rail 330; in other embodiments, clamping assembly 120 may be infinitely repositionable along rail 330. In some embodiments, clamping assembly 120 may be slid off the end of rail 330 and thus fully disconnected from rail 330 even after body component 430 and base component 410 are secured together. In other embodiments, clamping assembly 120 may be slid between two locations along rail 330 but a retaining element may prevent clamping assembly 120 from sliding off the end of rail 330 after body component 430 and base component 410 are secured together.

In its unlocked state, clamping assembly 120 may also be repositioned rotationally after body component 430 and base component 410 are secured together. Such rotational repositioning allows for varying the angle at which a stabilizing rod inserted in channel 450 is positioned relative to rail 330. In the embodiment shown in FIG. 4, the degree of possible rotational repositioning depends on the difference between the width of rail 330 and the distance between connection elements 470. The smaller the width of rail 330 relative to the distance between connection elements 470, the more rotational repositioning is possible. In some embodiments, clamping assembly 120 may be rotationally repositioned in a finite number of positions; in other embodiments, clamping assembly 120 may be infinitely rotationally repositioned.

Both the lateral and rotational position of clamping assembly 120 may be locked by introducing a stabilizing rod (not shown) into channel 450. Locking threads 460 prevent the stabilizing rod from exiting channel 450, and in some embodiments a locking nut, locking cap, or other component (not shown) may be employed to secure the stabilizing rod in channel 450. In some embodiments, clamping assembly 120 is still fully or partially adjustable after the insertion of the stabilizing rod, but not after the stabilizing rod is fully secured. Exemplary apparatus that may be utilized to lock the rod within channel 450 are described in U.S. Pat. No. 6,540,748 and U.S. Published Patent Application Nos. 2010/0256681 and 2006/0235392, each of which is owned by Blackstone Medical, Inc. and are hereby incorporated by reference.

A secured stabilizing rod in channel 450 contacts and exerts a force upon locking component 440, causing locking component 440 to exert a force upon the top surface of rail 330, pulling frictional surface 420 of clamping assembly base component 410 into contact with frictional surface 340 of rail 330. This immobilizing force locks the position of clamping assembly 120 both laterally and rotationally, effectively locking the position of the stabilizing rod relative to the occipital plate with no direct contact between the stabilizing rod and frictional surface 340. In the embodiment of FIG. 4, locking component 440 is a rod-to-plate locking pin located between clamping assembly body component 430 and rail 330. When a rod is inserted in clamping assembly 120, the rod presses on the locking pin causing pressure on rail 330, thus pulling the frictional surface of clamping assembly 120 into the frictional surface of rail 330, thus locking the rod to the rail.

Figure 5:
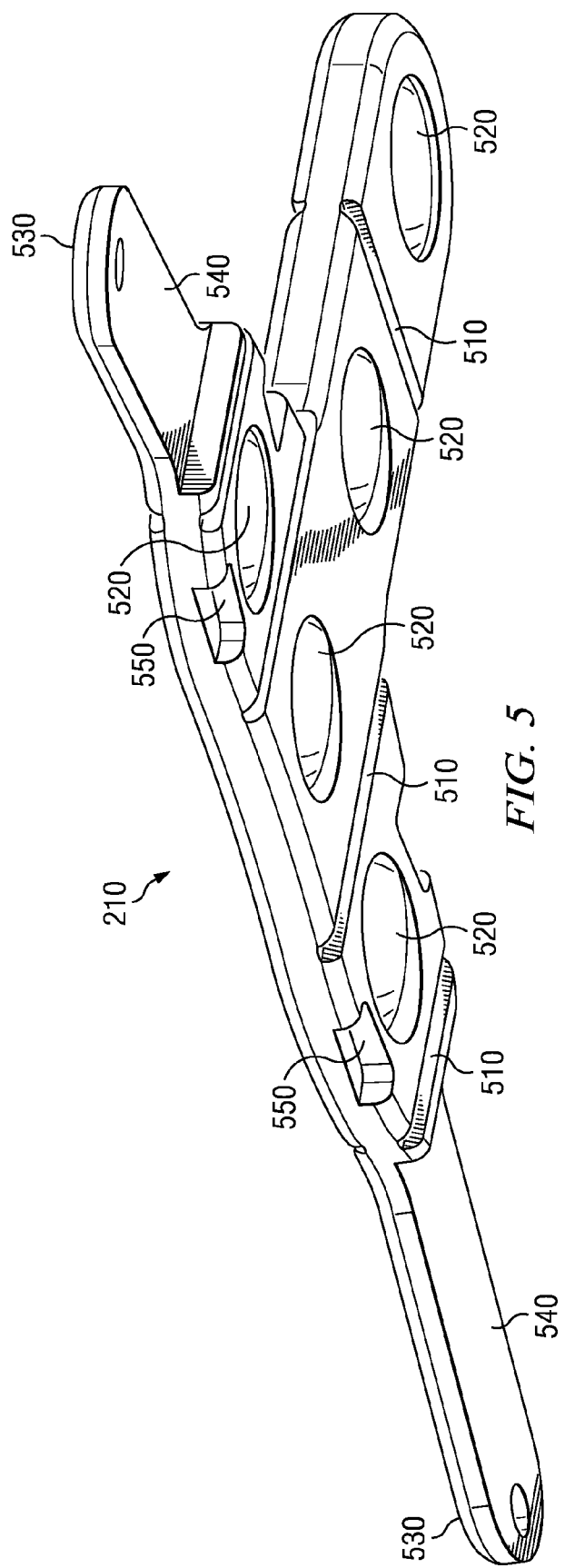
FIG. 5 illustrates an embodiment of an occipital plate component of an implantable occipito-cervical fixation assembly.

An embodiment of occipital plate 210 is illustrated in FIG. 5. Occipital plate 210 may be of any size and shape appropriate for securing to an occiput, and may be made from any material suitable for implantation into the body, such as stainless steel, titanium, ceramic, or a composite material. Grooves 510 may be scored into the top and/or bottom surfaces of occipital plate 210 to provide for easier and more precise contouring and reshaping of occipital plate 210. Such grooves 510 may allow better correlation with the surface of the occiput. Grooves 510 may be of varying length, width, and depth, and may run laterally, longitudinally, or in any other direction. Although FIG. 5 illustrates occipital plate 210 with multiple grooves 510, an occipital plate 210 with a single groove 510 or no grooves 510 is contemplated.

As shown in FIG. 5, multiple apertures 520 may be located on occipital plate 210. One or more such apertures may be arranged in any configuration across occipital plate 210. Such apertures may penetrate both the top and bottom surfaces of occipital plate 210, and may provide for attachment of occipital plate 210 to the occiput with bone fasteners (not shown) such as bone screws, pins, staples, or any other appropriate fasteners. An aperture 520 may be circular, oval, polygonal, or any other shape about a center axis. Furthermore, the center axis of an aperture 520 may be orthogonal to the surface of occipital plate 210, such that a bone faster seated within aperture 520 enters the occiput orthogonally, or the center axis of an aperture 520 may be non-orthogonal to the surface of occipital plate 210, such that a bone faster seated within aperture 520 enters the occiput at an acute angle, providing for more contact between bone and fastener. In addition, aperture 520 may be countersunk such that the head of a bone fastener seated within aperture 520 is flush with or recessed from the top surface of occipital plate 210. Aperture 520 may also be counter-bored or otherwise shaped to accommodate a variety of bone fasteners. Multiple apertures 520 distributed across occipital plate 210 may be of uniform size and shape or may be of variable size and shape.

It is contemplated that occipital plate 210 may not utilize any apertures 520. In such embodiments, other methods of securing the occipital plate to the occiput are employed. For example, the occipital plate may be secured to the occiput with an adhesive, or fixation elements that penetrate the occiput may be integrated with the occipital plate, thereby eliminating the need for separate bone fasteners. Furthermore, notches 550 or other guide features for interfacing with instruments external to occipital plate 210 may be located on occipital plate 210. Such instrument interfaces may allow a tool to be attached to facilitate placement, adjustment, and other manipulation of occipital plate 210.

As shown in FIG. 5, a rail 530 for supporting a clamping assembly extends laterally from each side of occipital plate 210. Apertures 520 may be located on the distal portion of occipital plate 210, laterally extending rails 530 may be located proximally. Although FIG. 5 illustrates an embodiment with two laterally extending rails, embodiments with a single rail and embodiments with three or more rails are contemplated. Frictional surface 540 is provided on the bottom surface of each laterally extending rail 530. In some embodiments, frictional surface 540 may be recessed relative to the bottom surface of rail 530 and/or relative to the bottom surface of occipital plate 210.

Figure 6A:
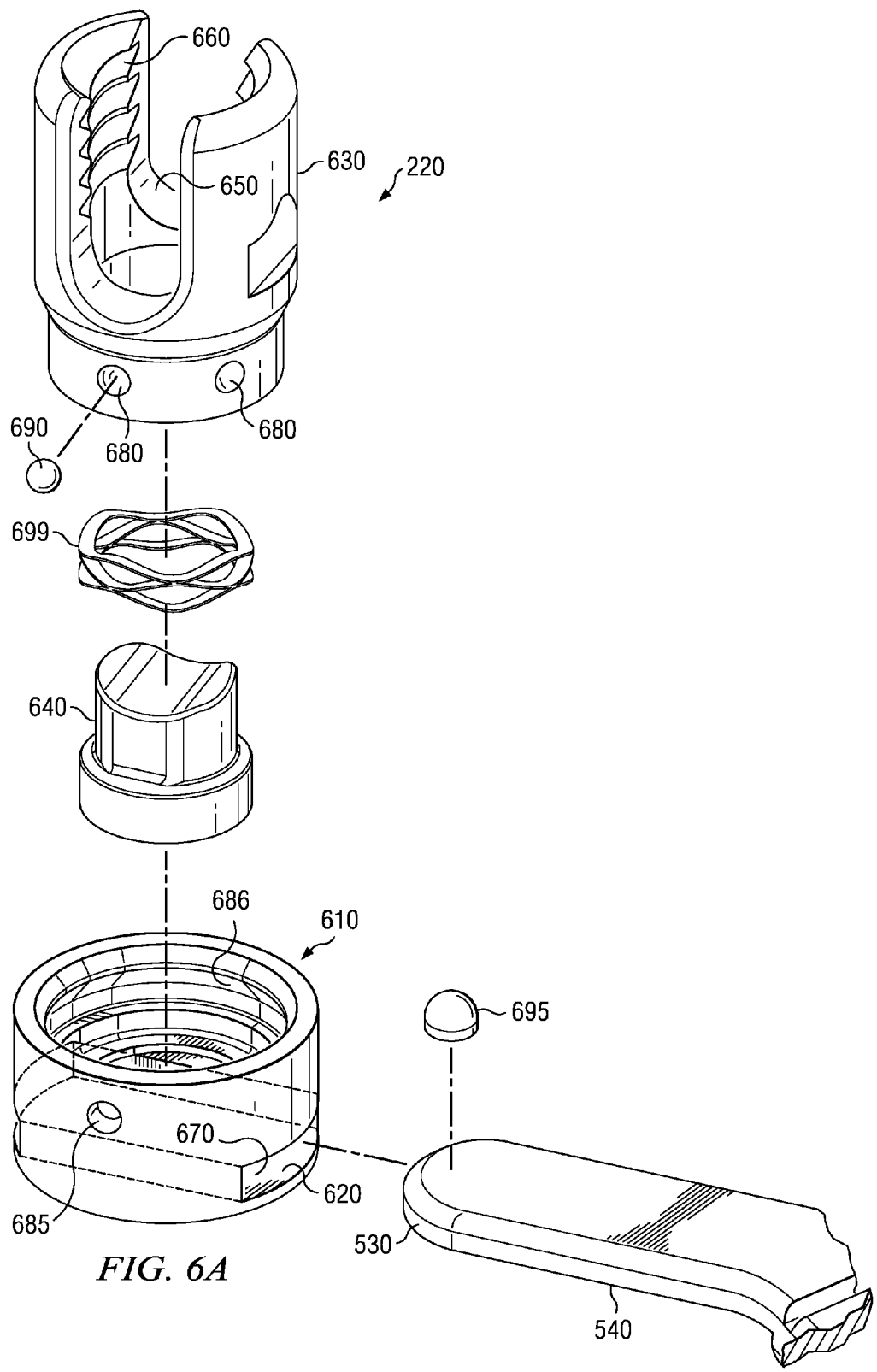
FIG. 6A illustrates an embodiment of a clamping assembly component of an implantable occipito-cervical fixation assembly.
Figure 6B:
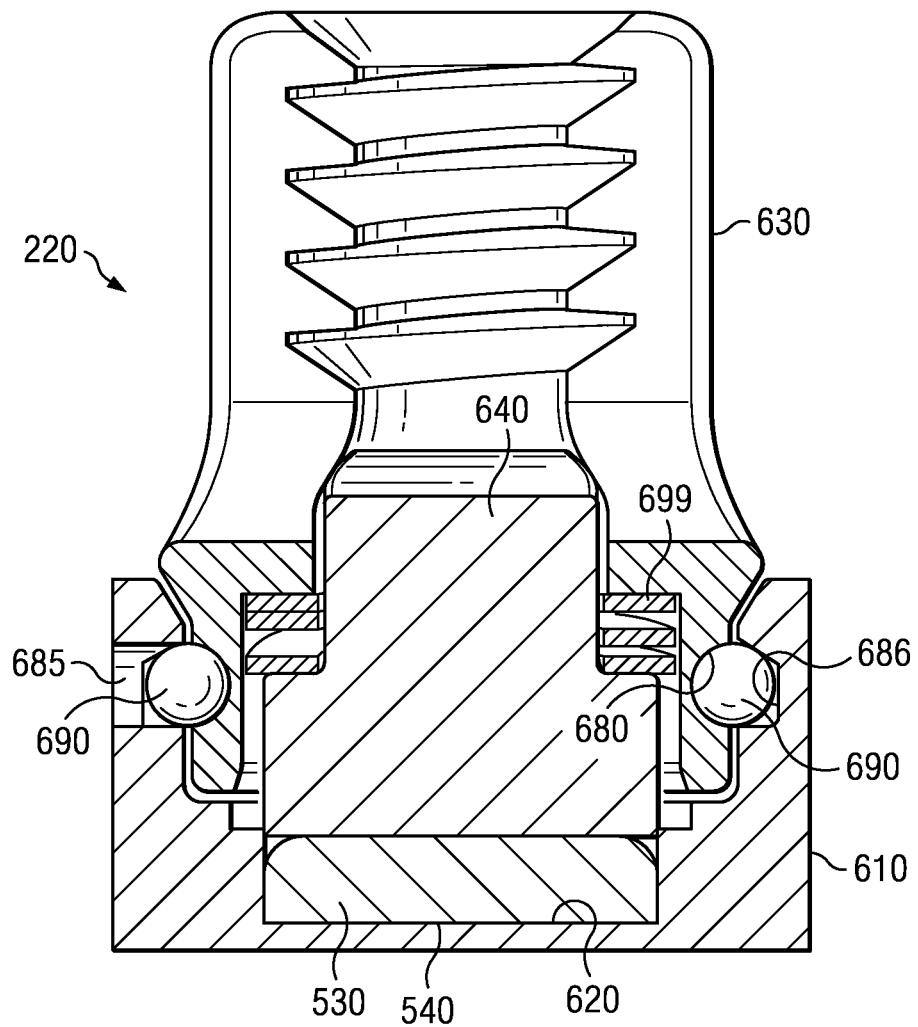
FIG. 6B illustrates a cross-sectional view of an embodiment of a clamping assembly component of an implantable occipito-cervical fixation assembly.

An embodiment of clamping assembly 220 is illustrated in FIG. 6A. A cross-sectional view of this embodiment is illustrated in FIG. 6B. Clamping assembly 220 may be of any size and shape appropriate for securing a stabilizing rod to an occipital plate, and may be made from any material suitable for implantation into the body, such as stainless steel, titanium, ceramic, or a composite material. Clamping assembly base component 610 comprises frictional surface 620, opening 685 into ball channel 686, and aperture 670. Clamping assembly body component 630 comprises channel 650, dimples 680, and locking threads 660. To construct an embodiment of clamping assembly 220, rail 530 may be inserted through clamping assembly base component aperture 670 such that frictional surface 620 of clamping assembly base component 610 is in contact with frictional surface 540 of rail 530. Locking component 640 may be positioned within a receptacle of body component 630. According to one embodiment, the locking component may have a saddle-shaped surface adapted for contacting the stabilizing rod with a larger surface area than a rounded surface. Body component 630 may then be united with base component 610 such that locking component 640 contacts rail 530. Dimple 680 may then be aligned with opening 685 of clamping assembly base component 610 for insertion of a ball 690 into ball channel 686. Body component 630 may then be rotated until the next dimple 680 is aligned with opening 685 for insertion of another ball 690 until each dimple 680 is occupied by a ball 690. Each of the balls 690 may interface with the ball channel 686 once it has been installed into the body component 630, thereby allowing the body component to rotate with respect to the base component 610. Once all of the balls 690 have been installed, a cap or closing screw may be inserted into opening 685, thus preventing the balls 690 from falling out of the clamping assembly 220 during rotational movement of the body component 630 with respect to the base component 610.

As constructed, clamping assembly 220 in its unlocked state loosely encloses a portion of rail 530 and may be repositioned by sliding clamping assembly 220 along a portion of rail 530. In some embodiments, clamping assembly 220 may be repositioned at discrete points along rail 530; in other embodiments, clamping assembly 220 may be infinitely repositionable along rail 530. In some embodiments, clamping assembly 220 may be slid off the end of rail 530 and thus fully disconnected from rail 530 even after body component 630 and base component 610 are secured together. In other embodiments, clamping assembly 220 may be slid between two locations along rail 530 but a retaining element 695 may prevent clamping assembly 220 from sliding off the end of rail 530.

In its unlocked state, clamping assembly 220 may also be repositioned rotationally after body component 630 and base component 610 are secured together. Such rotational repositioning allows for varying the angle at which a stabilizing rod inserted in channel 650 is positioned relative to rail 530. In the embodiment shown in FIGS. 6A and 6B, the method of securing body component 630 to base component 610 provides for infinite rotational repositioning, since ball channel 686 allows body component 630 to freely rotate within base component 610. In some embodiments, clamping assembly 220 may be rotationally repositioned in a finite number of positions. In some embodiments, clamping assembly 220 may be infinitely rotationally repositioned within a limited range.

Both the lateral and rotational position of clamping assembly 220 may be locked by introducing a stabilizing rod (not shown) into channel 650. Locking threads 660 prevent the stabilizing rod from exiting channel 650, and in some embodiments a locking nut, locking cap, or other component (not shown) may be employed to secure the stabilizing rod in channel 650. In some embodiments, clamping assembly 220 is still fully or partially adjustable after the insertion of the stabilizing rod, but not after the stabilizing rod is fully secured.

A secured stabilizing rod in channel 650 contacts and exerts a force upon locking component 640, causing locking component 640 to exert a force upon the top surface of rail 530, pulling frictional surface 620 of clamping assembly base component 610 into contact with frictional surface 540 of rail 530. This immobilizing force locks the position of clamping assembly 220 both laterally and rotationally, effectively locking the position of the stabilizing rod relative to the occipital plate with no contact between the stabilizing rod and frictional surface 540. In the embodiment of FIGS. 6A and 6B, locking component 640 is a rod-to-plate locking pin located between clamping assembly body component 630 and rail 530. When a rod is inserted in clamping assembly 220, the rod presses on the locking pin causing pressure on rail 530, thus pulling the frictional surface of clamping assembly 220 into contact with the frictional surface of rail 530, thus locking the rod to the rail.

In some embodiments, a loading component may exert a stabilizing force on the locking component to keep the clamping assembly positionally stable prior to locking. Such a loading component allows for more precise lateral and rotational positioning of the clamping assembly. In the embodiment illustrated in FIGS. 6A and 6B, loading component 699 is represented by a wave spring located between clamping assembly body component 630 and locking component 640. The wave spring exerts a light pressure on locking component 640 to act as a load to the system. This load imparts a friction to the system, keeping the clamping assembly positionally stable. Although a wave spring is depicted in FIGS. 6A and 6B, other suitable methods of loading the system are contemplated.

According to some embodiments, the disclosed assembly may be connected to one or more rods that are also connected to one or more cervical vertebrae. These rods may be connected to the cervical vertebra through the use of pedicle screws, such as the screws described in U.S. Pat. No. 6,540,748 and U.S. Published Patent Application No. 2010/0256681, both of which are owned by Blackstone Medical, Inc. and which are incorporated herein by reference.

Although the present invention has been described in detail, it should be understood that various changes, substitutions, and alterations can be made without departing from the spirit and scope of the invention as defined by the appended claims. Various terms used herein have special meanings within the present technical field. Whether a particular term should be construed as such a "term of art" depends on the context in which that term is used. "Connected to," "coupled to," "secured to," "in contact with," or other similar terms should generally be construed broadly. These and other terms are to be construed in light of the context in which they are used in the present disclosure and as those terms would be understood by one of ordinary skill in the art would understand those terms in the disclosed context. The above definitions are not exclusive of other meanings that might be imparted to those terms based on the disclosed context.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

We claim:

1. An implantable orthopedic assembly comprising:
   an occipital plate comprising a top surface and a bottom surface, the bottom surface of the occipital plate adapted for securing to an occiput;
   at least one rail extending laterally from a proximal portion of the occipital plate, the at least one rail comprising a top surface and a bottom surface, the bottom surface of the rail comprising a frictional surface; and
   at least one repositionable clamping assembly adapted to enclose a portion of the at least one rail, the clamping assembly further adapted for securing a portion of a stabilizing rod at a distance from the frictional surface of the at least one rail, the clamping assembly comprising:
      a base component comprising a frictional surface, the frictional surface of the base component adapted to contact the frictional surface of the at least one rail, the base component further adapted for lateral repositioning between a first rail position and a second rail position;
      a body component adapted to be rigidly coupled to the base component, the body component further adapted for repositioning between a first rotational position and a second rotational position, the body component further adapted to receive the portion of the stabilizing rod; and
      a locking component adapted to contact the body component when the body component is in contact with the top surface of the at least one rail, and is also in contact with the received portion of the stabilizing rod, the locking component adapted to transfer an immobilizing force from the received portion of the stabilizing rod to the top surface of the at least one rail, the immobilizing force immobilizing the clamping assembly at a fixed rail position and in a fixed rotational position.

2. The implantable orthopedic assembly of claim 1, wherein the occipital plate further comprises at least one groove scoring at least one of the top surface of the occipital plate or the bottom surface of the occipital plate, the at least one groove adapted to facilitate contouring of the occipital plate.

3. The implantable orthopedic assembly of claim 2, wherein the at least one groove comprises a first groove and a second groove, the second groove substantially orthogonal to the first groove.

4. The implantable orthopedic assembly of claim 1, wherein a plurality of apertures is variably distributed across the occipital plate, wherein the plurality of apertures penetrates both the top surface of the occipital plate and the bottom surface of the occipital plate, and wherein at least one of the plurality of apertures is adapted to receive at least one bone fastener, the at least one bone fastener adapted to secure the bottom surface of the occipital plate to the occiput.

5. The implantable orthopedic assembly of claim 4, wherein the at least one bone fastener comprises a bone screw.

6. The implantable orthopedic assembly of claim 4, wherein the plurality of apertures comprises a substantially circular first aperture centered about a first aperture center axis.

7. The implantable orthopedic assembly of claim 6, wherein the first aperture center axis is non-orthogonal to at least one of the top surface of the occipital plate and the bottom surface of the occipital plate.

8. The implantable orthopedic assembly of claim 4, wherein at least one of the plurality of apertures comprises a countersunk aperture.

9. The implantable orthopedic assembly of claim 1, the occipital plate further comprising at least one instrument interface adapted to facilitate manipulation of the occipital plate with an instrument.

10. The implantable orthopedic assembly of claim 9, wherein the occipital plate further comprises an edge surface connecting the top surface of the occipital plate and the bottom surface of the occipital plate, and wherein the at least one instrument interface comprises a notch in the edge surface of the occipital plate.

11. The implantable orthopedic assembly of claim 1, wherein the at least one rail comprises a first rail and a second rail, the first rail extending from a left side of the occipital plate, the second rail extending from a right side of the occipital plate.

12. The implantable orthopedic assembly of claim 1, wherein the frictional surface of the at least one rail is recessed.

13. The implantable orthopedic assembly of claim 1, wherein the base component of the at least one repositionable clamping assembly is adapted for infinite lateral repositioning between the first rail position and the second rail position.

14. The implantable orthopedic assembly of claim 1, wherein the body component of the at least one repositionable clamping assembly is adapted for infinite rotational repositioning between the first body position and the second body position.

15. The implantable orthopedic assembly of claim 1, wherein the at least one repositionable clamping assembly further comprises a loading component adapted to exert a stabilizing force on the locking component, the stabilizing force stabilizing the at least one repositionable clamping assembly at an adjustable rail position and in an adjustable body position.

16. The implantable orthopedic assembly of claim 1, wherein the base component comprises at least one element adapted to be connected to at least one corresponding protrusion from the body component.

17. The implantable orthopedic assembly of claim 16, wherein the body component comprises two protrusions adapted to be placed on opposite sides of the at least one rail and the base component comprises two corresponding receiving elements into which the protrusions may be attached.

18. The implantable orthopedic assembly of claim 17, wherein the protrusions are attached to the receiving elements by a weld.

19. The implantable orthopedic assembly of claim 17, wherein the locking component has a rounded upper surface for contacting the received portion of the stabilizing rod.

20. The implantable orthopedic assembly of claim 1, wherein the base component comprises an aperture that is adapted to enclose a portion of the at least one rail.

21. The implantable orthopedic assembly of claim 1, wherein the clamping assembly further comprises a loading device adapted to be positioned between the body component and the locking component.

22. The implantable orthopedic assembly of claim 21, wherein the loading device comprises a wave spring.

23. The implantable orthopedic assembly of claim 1, wherein the base component comprises a radial channel on the interior surface of the base component and an opening aligned with the channel, and wherein the body component comprises at least one dimple positioned on the outer surface such that when the base component is connected to the body component, the at least one dimple can be aligned with the opening in the base component.

24. The implantable orthopedic assembly of claim 23, further comprising at least one ball corresponding to each of the at least one dimples, each of said balls adapted to be placed into the opening and mated with a corresponding dimple when the base component is connected to the body component, and further wherein the ball facilitates rotational movement of the body component with respect to the base component by moving within the radial channel of the base component while remaining adjacent to the corresponding dimple in the body component.

25. The implantable orthopedic assembly of claim 1, wherein the locking component has a saddle-shaped surface for contacting the received portion of the stabilizing rod.

26. The implantable orthopedic assembly of claim 20, further comprising a retaining element that is adapted to be attached to the rail and prevent the base component from sliding off an end of the rail.

27. A method of constructing an implantable orthopedic assembly comprising an occipital plate, at least one rail rigidly coupled to and extending laterally from the occipital plate, and at least one repositionable clamping assembly enclosing a portion of the at least one rail, the at least one repositionable clamping assembly adapted for securing a received portion of a stabilizing rod, the method comprising:

positioning a locking component of the repositionable clamping assembly within a receptacle of a body component of the at least one repositionable clamping assembly;

positioning a frictional surface of the at least one rail against a frictional surface of a base component of the at least one repositionable clamping assembly;

uniting the body component with the base component, wherein the at least one rail contacts the locking component; and securing the base component to the body component.

28. The method of claim 27, further comprising positioning a loading component between the locking component and the body component of the at least one repositionable clamping assembly, wherein the loading component is adapted to exert a bias on the locking component against the at least one rail to stabilizing the at least one repositionable clamping assembly at an adjustable rail position and in an adjustable body position.

\* \* \* \* \*